United States Patent
Ha et al.

(10) Patent No.: US 10,143,591 B2
(45) Date of Patent: Dec. 4, 2018

(54) LOW PROFILE EUSTACHIAN TUBE DILATION SYSTEM

(71) Applicant: Acclarent, Inc., Menlo Park, CA (US)

(72) Inventors: Hung V. Ha, San Jose, CA (US);
Ketan P. Muni, San Jose, CA (US);
Andrew Nguyen, San Jose, CA (US);
Siddhi K. Desai, San Jose, CA (US);
Ronak Muni, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 216 days.

(21) Appl. No.: 14/851,022

(22) Filed: Sep. 11, 2015

(65) Prior Publication Data
US 2016/0081857 A1   Mar. 24, 2016

Related U.S. Application Data

(60) Provisional application No. 62/049,267, filed on Sep. 11, 2014.

(51) Int. Cl.
*A61F 11/00* (2006.01)
*A61B 1/00* (2006.01)
(Continued)

(52) U.S. Cl.
CPC ........ *A61F 11/004* (2013.01); *A61B 1/00082* (2013.01); *A61B 1/233* (2013.01);
(Continued)

(58) Field of Classification Search
CPC ... A61B 1/00082; A61B 1/227; A61B 1/2275; A61B 1/233; A61F 11/00; A61F 11/002; A61F 11/004; A61F 13/2017; A61F 2/18; A61F 2/958; A61F 2002/183; A61M 2025/1081; A61M 25/10
See application file for complete search history.

(56) References Cited

U.S. PATENT DOCUMENTS 1,650,959 A * 11/1927 Pitman .................. A61B 1/233
                                                       600/153
1,735,519 A * 11/1929 Vance ................... A61M 29/02
                                                       601/148

(Continued)

FOREIGN PATENT DOCUMENTS

WO    WO 93/21816 A1    11/1993
WO    WO 2013/155409 A1    10/2013

OTHER PUBLICATIONS

International Search Report dated Nov. 17, 2015, International Application No. PCT/US2015/048811.
(Continued)

*Primary Examiner* — Ryan J Severson (57) ABSTRACT

A system and method for dilating a Eustachian tube of a patient is disclosed. The device includes a protective sheath, a flexible endoscope and a balloon dilation catheter. The protective sheath includes an endoscope lumen and a balloon dilation catheter lumen. The balloon of the balloon dilation catheter is a low profile balloon particularly useful for dilating the Eustachian tube, and in particular, the Eustachian tube of a pediatric patient. The method involves advancing the balloon dilation catheter through a nasal passage of the patient to dilate a portion of the Eustachian tube.

8 Claims, 9 Drawing Sheets

(51) Int. Cl.
*A61B 1/233* (2006.01)
*A61F 2/958* (2013.01)
*A61M 29/02* (2006.01)

(52) U.S. Cl.
CPC ............. *A61F 11/002* (2013.01); *A61F 2/958* (2013.01); *A61M 29/02* (2013.01); *A61M 2029/025* (2013.01)

(56) References Cited

U.S. PATENT DOCUMENTS

| | | | | |
|---|---|---|---|---|
| 5,331,947 | A * | 7/1994 | Shturman | A61B 8/12 600/106 |
| 7,654,997 | B2 * | 2/2010 | Makower | A61B 17/24 604/509 |
| 7,771,409 | B2 * | 8/2010 | Chang | A61B 17/24 604/514 |
| 7,803,150 | B2 * | 9/2010 | Chang | A61B 17/24 604/514 |
| 8,090,433 | B2 * | 1/2012 | Makower | A61B 1/00135 600/510 |
| 8,425,457 | B2 * | 4/2013 | John | A61B 17/24 604/101.01 |
| 8,715,169 | B2 * | 5/2014 | Chang | A61B 17/24 600/116 |
| 8,764,726 | B2 * | 7/2014 | Chang | A61B 17/24 604/509 |
| 8,828,041 | B2 * | 9/2014 | Chang | A61B 17/24 606/196 |
| 8,858,586 | B2 * | 10/2014 | Chang | A61B 17/24 606/196 |
| 8,951,225 | B2 * | 2/2015 | Evard | A61M 25/10 604/96.01 |
| 9,055,965 | B2 * | 6/2015 | Chang | A61B 17/24 |
| 9,220,879 | B2 * | 12/2015 | Chang | A61B 17/24 |
| 9,370,649 | B2 * | 6/2016 | Chang | A61B 17/24 |
| 9,399,121 | B2 * | 7/2016 | Goldfarb | A61M 25/0041 |
| 2005/0240147 | A1 * | 10/2005 | Makower | A61B 17/24 604/96.01 |
| 2006/0210605 | A1 * | 9/2006 | Chang | A61B 17/24 424/434 |
| 2007/0135789 | A1 * | 6/2007 | Chang | A61B 17/24 604/500 |
| 2007/0208301 | A1 * | 9/2007 | Evard | A61M 25/10 604/103.1 |
| 2008/0097295 | A1 * | 4/2008 | Makower | A61B 17/24 604/99.04 |
| 2008/0125626 | A1 * | 5/2008 | Chang | A61B 17/24 600/104 |
| 2008/0154250 | A1 * | 6/2008 | Makower | A61B 17/24 606/10 |
| 2008/0195041 | A1 * | 8/2008 | Goldfarb | A61M 29/02 604/96.01 |
| 2008/0275483 | A1 * | 11/2008 | Makower | A61B 17/24 606/192 |
| 2009/0093823 | A1 * | 4/2009 | Chang | A61B 17/24 606/110 |
| 2009/0163890 | A1 * | 6/2009 | Clifford | A61B 1/227 604/514 |
| 2009/0312745 | A1 * | 12/2009 | Goldfarb | A61M 25/0041 604/514 |
| 2010/0042046 | A1 * | 2/2010 | Chang | A61B 17/24 604/96.01 |
| 2010/0100181 | A1 * | 4/2010 | Makower | A61B 17/24 623/10 |
| 2010/0174138 | A1 * | 7/2010 | Chang | A61B 17/24 600/104 |
| 2010/0174308 | A1 * | 7/2010 | Chang | A61B 17/24 606/199 |
| 2010/0198191 | A1 * | 8/2010 | Clifford | A61B 1/227 604/514 |
| 2010/0210901 | A1 * | 8/2010 | Makower | A61B 17/24 600/104 |
| 2010/0274188 | A1 * | 10/2010 | Chang | A61B 1/227 604/96.01 |
| 2011/0004057 | A1 * | 1/2011 | Goldfarb | A61B 1/233 600/106 |
| 2011/0060214 | A1 * | 3/2011 | Makower | A61B 5/6851 600/424 |
| 2011/0160740 | A1 * | 6/2011 | Makower | A61B 17/24 606/115 |
| 2012/0245419 | A1 * | 9/2012 | Makower | A61B 17/24 600/146 |
| 2013/0231529 | A1 * | 9/2013 | John | A61B 17/24 600/104 |
| 2014/0107427 | A1 * | 4/2014 | Chow | A61B 17/24 600/249 |
| 2014/0296898 | A1 * | 10/2014 | Chang | A61B 17/24 606/170 |
| 2014/0324093 | A1 * | 10/2014 | Chang | A61B 17/24 606/196 |
| 2015/0165175 | A1 * | 6/2015 | Evard | A61M 25/10 606/196 |
| 2015/0202089 | A1 * | 7/2015 | Campbell | A61F 11/002 600/478 |
| 2015/0209055 | A1 * | 7/2015 | Chang | A61B 17/24 600/424 |
| 2016/0081857 | A1 * | 3/2016 | Ha | A61B 1/00082 600/106 |
| 2016/0287445 | A1 * | 10/2016 | Wasicek | A61M 25/10184 |
| 2017/0007281 | A1 * | 1/2017 | Goldfarb | A61M 25/0041 |
| 2017/0119993 | A1 * | 5/2017 | Desai | A61M 19/00 |

OTHER PUBLICATIONS

Written Opinion of the International Searching Authority, International Application No. PCT/US2015/048811.
International Preliminary Report on Patentability dated Mar. 14, 2017, International Application No. PCT/US2015/048811.

* cited by examiner

LOW PROFILE EUSTACHIAN TUBE DILATION SYSTEM

FIELD OF THE INVENTION

The present invention is related to methods and systems for accessing and treating target tissue regions within the middle ear and the Eustachian tube.

BACKGROUND OF THE INVENTION

Figure 1:
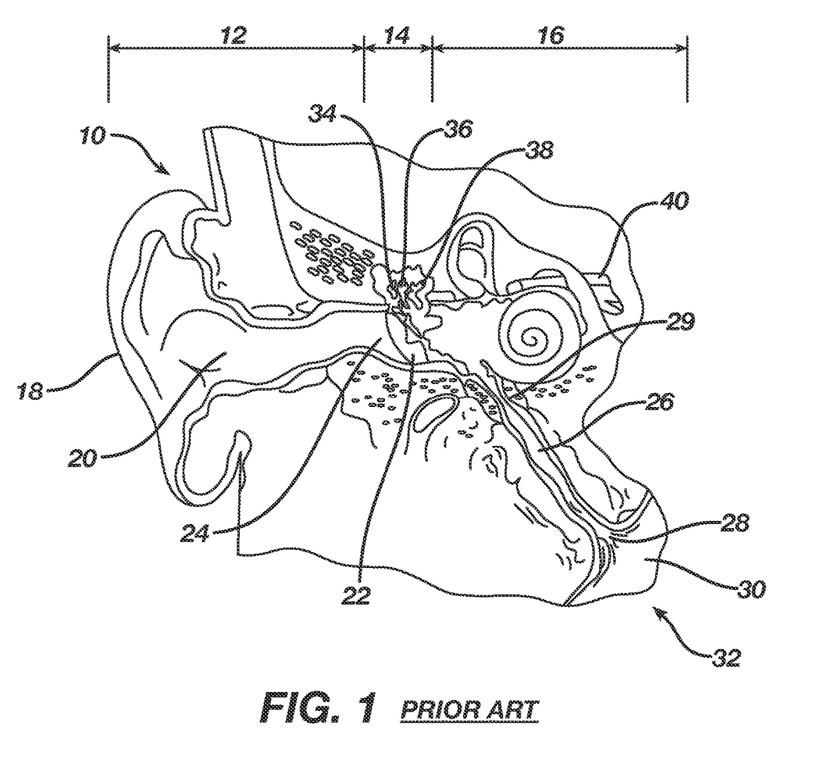
FIG. 1 is a cross-section of a human ear showing the inner, middle and outer ear portions and the Eustachian tube connecting the middle ear with the nasopharynx region of the throat via a distal opening thereof.
Figure 2:
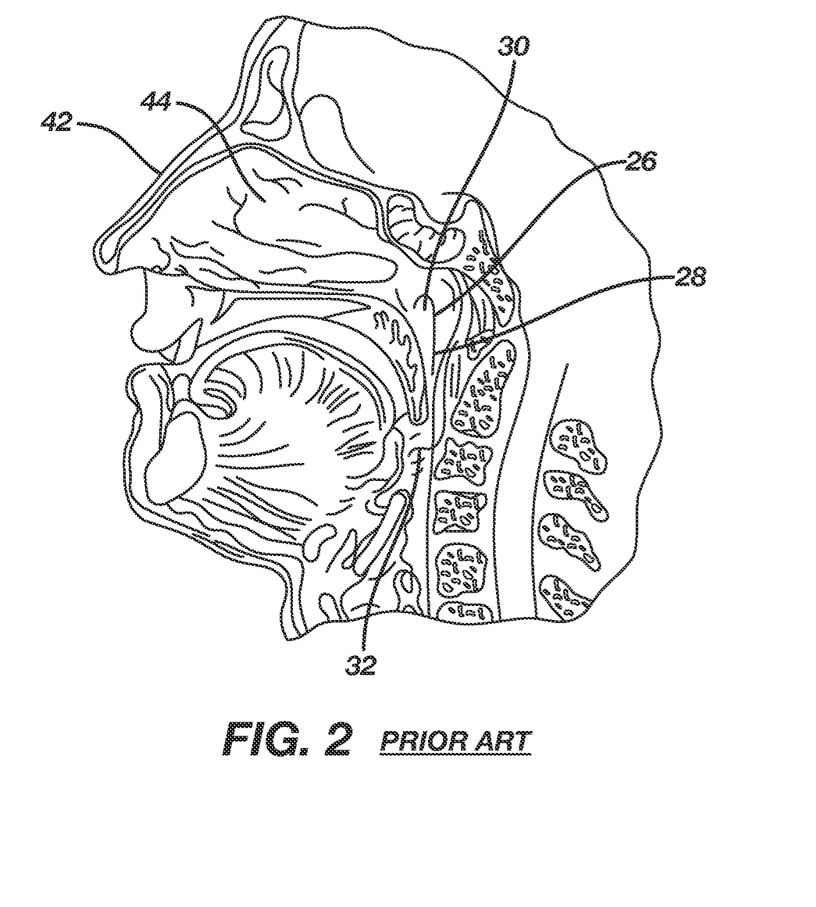
FIG. 2 is a cross-section of a human head showing the nasopharynx region of the throat illustrated in FIG. 1 containing the distal opening of the Eustachian tube illustrated in FIG. 1.

Referring to FIGS. 1-2, the ear 10 is divided into three parts: an external ear 12, a middle ear 14 and an inner ear 16. The external ear 12 consists of an auricle 18 and ear canal 20 that gather sound and direct it towards a tympanic membrane 22 (also referred to as the eardrum) located at an inner end 24 of the ear canal 20. The middle ear 14 lies between the external and inner ears 12 and 16 and is connected to the back of the throat by a Eustachian tube 26 which serves as a pressure equalizing valve between the ear 10 and the sinuses. The Eustachian tube 26 terminates in a distal opening or ostium 28 in the nasopharynx region 30 of the throat 32. In addition to the eardrum 22, the middle ear 14 also consists of three small ear bones (ossicles): the malleus 34 (hammer), incus 36 (anvil) and stapes 38 (stirrup). These bones 34-38 transmit sound vibrations to the inner ear 16 and thereby act as a transformer, converting sound vibrations in the canal 20 of the external ear 12 into fluid waves in the inner ear 16. These fluid waves stimulate several nerve endings 40 that, in turn, transmit sound energy to the brain where it is interpreted.

The Eustachian tube 26 is a narrow, two to two-and-a-half centimeter long channel, measured from the ostium 28 to the bony isthmus 29, connecting the middle ear 14 with the nasopharynx 30, the upper throat area just above the palate, in back of the nose. The Eustachian tube 26 functions as a pressure equalizing valve for the middle ear 14 which is normally filled with air. When functioning properly, the Eustachian tube 26 opens for a fraction of a second periodically (about once every three minutes) in response to swallowing or yawning. In so doing, it allows air into the middle ear 14 to replace air that has been absorbed by the middle ear lining (mucous membrane) or to equalize pressure changes occurring on altitude changes. Anything that interferes with this periodic opening and closing of the Eustachian tube 26 may result in hearing impairment or other ear symptoms. Obstruction or blockage of the Eustachian tube 26 results in a negative middle ear pressure 14, with retraction (sucking in) of the eardrum 22. In adults, this is usually accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear 14, creating a condition referred to as serous otitis media (fluid in the middle ear). This occurs frequently in children in connection with an upper respiratory infection and accounts for the hearing impairment associated with this condition.

A lining membrane (mucous membrane) of the middle ear 14 and Eustachian tube 26 is connected with, and is the same as, the membrane of the nose 42, sinuses 44 and throat 32. Infection of these areas results in mucous membrane swelling which in turn may result in obstruction of the Eustachian tube 26. This is referred to as serous otitis media, i.e. essentially a collection of fluid in the middle ear 14 that can be acute or chronic, usually the result of blockage of the distal opening 28 of the Eustachian tube 26 which allows fluid to accumulate in the middle ear 14. In the presence of bacteria, this fluid may become infected, leading to an acute suppurative otitis media (infected or abscessed middle ear). When infection does not develop, the fluid remains until the Eustachian tube 26 again begins to function normally, at which time the fluid is absorbed or drains down the tube into the throat 32 through the Eustachian tube opening 28.

Chronic serous otitis media may result from longstanding Eustachian tube blockage or from thickening of the fluid so that it cannot be absorbed or drained down the Eustachian tube 26. This chronic condition is usually associated with hearing impairment. There may be recurrent ear pain, especially when the individual catches a cold. Fortunately, serous otitis media may persist for many years without producing any permanent damage to the middle ear mechanism. The presence of fluid in the middle ear 14, however, makes it very susceptible to recurrent acute infections. These recurrent infections may result in middle ear damage.

When the Eustachian tube 26 contains a build-up of fluid, a number of things will occur. First, the body absorbs the air from the middle ear 14, causing a vacuum to form which tends to pull the lining membrane and ear drum 22 inward, causing pain. Next, the body replaces the vacuum with more fluid which tends to relieve the pain, but the patient can experience a fullness sensation in the ear 10. Treatment of this condition with antihistamines and decongestants can take many weeks to be fully effective. Finally, the fluid can become infected, which is painful and makes the patient feel ill and which may cause the patient not to be able to hear well. If the inner ear 14 is affected, the patient may feel a spinning or turning sensation (vertigo). The infection is typically treated with antibiotics.

However, even if antihistamines, decongestants and antibiotics are used to treat an infection or other cause of fluid build-up in the middle ear 14, these treatments will typically not immediately resolve the pain and discomfort caused by the buildup of fluid in the middle ear 14; i.e. the most immediate relief will be felt by the patient if the fluid can be removed from the Eustachian tube 26.

Antibiotic treatment of middle ear infections typically results in normal middle ear function within three to four weeks. During the healing period, the patient can experience varying degrees of ear pressure, popping, clicking and fluctuation of hearing, occasionally with shooting pain in the ear. Resolution of the infection occasionally leaves the patient with uninfected fluid in the middle ear 14, localized in the Eustachian tube 26.

Fluid build-up caused by these types of infections has been treated surgically in the past. The primary objective of surgical treatment of chronic serous otitis media is to reestablish ventilation of the middle ear, keeping the hearing at a normal level and preventing recurrent infection that might damage the eardrum membrane and middle ear bones.

Figure 3:
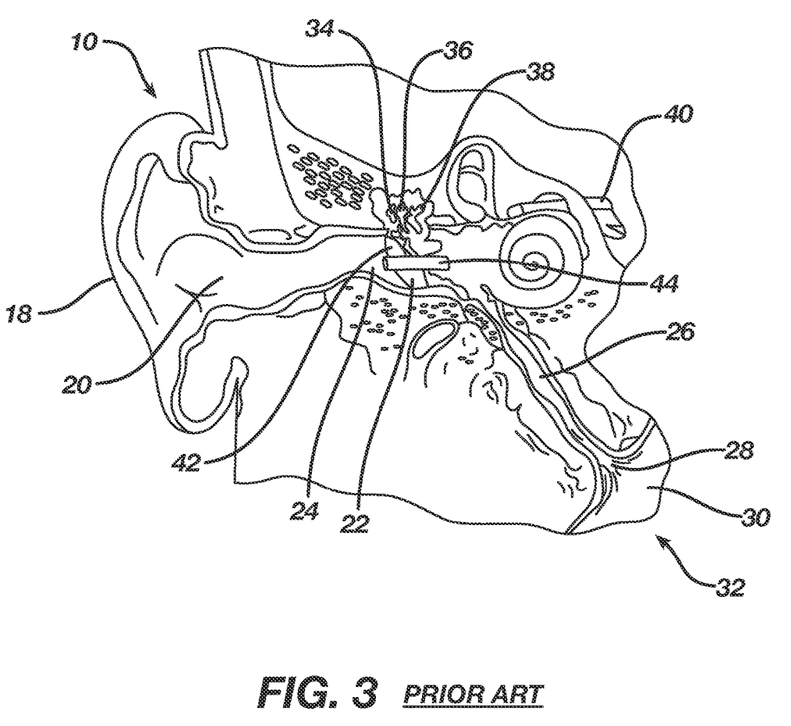
FIG. 3 is a cross-section of a human ear in the orientation shown in FIG. 1 showing a prior art surgical method for relieving fluid in the middle ear in which a ventilation tube is placed within an incision in the eardrum.

For example, as shown in FIG. 3, a myringotomy can be performed to relieve fluid in the middle ear 14. A myringotomy is an incision 42 in the eardrum 22 performed to remove fluid in the middle ear 14. A hollow plastic tube 44, referred to as a ventilation tube, is inserted and lodged in the incision 42 to prevent the incision 42 from healing and to ensure ventilation of the middle ear 14. The ventilation tube 44 temporarily takes the place of the Eustachian tube 26 in equalizing the pressure in the middle ear 14. The ventilation tube 44 usually remains in place for three to nine months during which time the Eustachian tube 26 blockage subsides. When the tube 44 dislodges, the eardrum 22 heals; the Eustachian tube 26 then resumes its normal pressure equalizing function.

Figure 4:
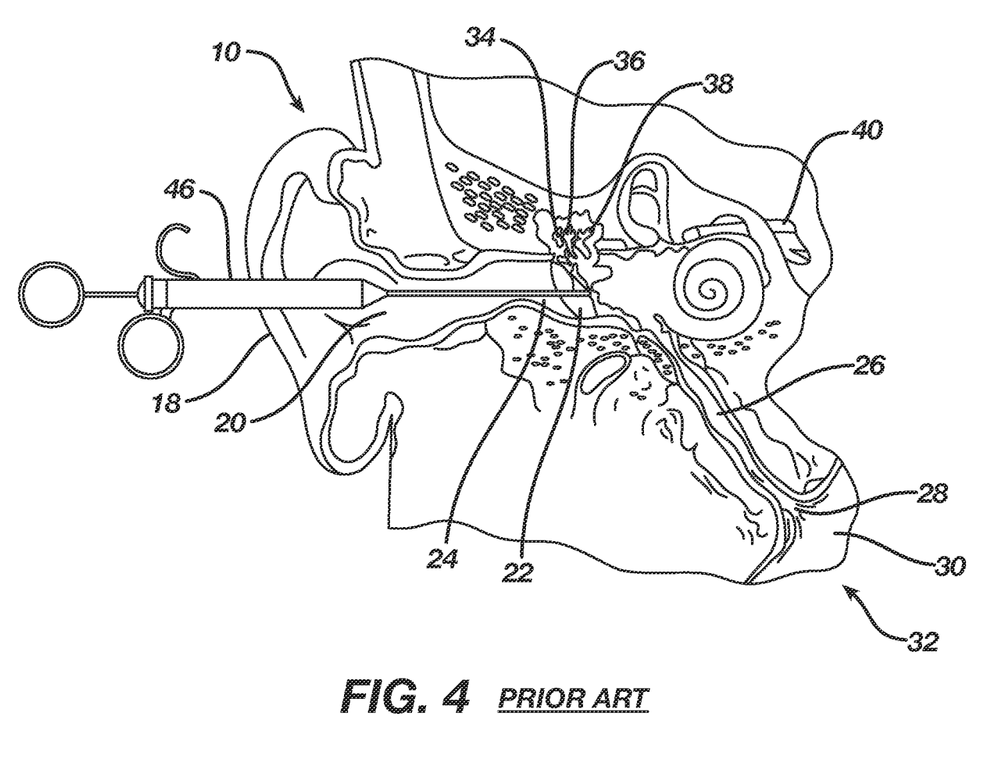
FIG. 4 is a cross-section of a human ear in the orientation shown in FIG. 1 showing a prior art surgical method for relieving fluid in the middle ear in which a syringe is shown having a needle perforating the eardrum.

Another method of relieving the pressure in the middle ear 14 is shown in FIG. 4 in which a hypodermic needle 46 is driven through the eardrum 22 through which any accumulated fluid can be withdrawn from typically only the upper portion of the Eustachian tube 26.

The methods of FIGS. 3 and 4 involve rupturing the eardrum 22 to relieve the fluid accumulation and pressure increase in the middle ear. Neither of these methods, in addition to the sometimes permanent puncture created in the eardrum 22, is especially effective in removing all of the fluid in the Eustachian tube 26 since often the lower end 28 thereof is blocked and dammed with fluid.

Figure 5:
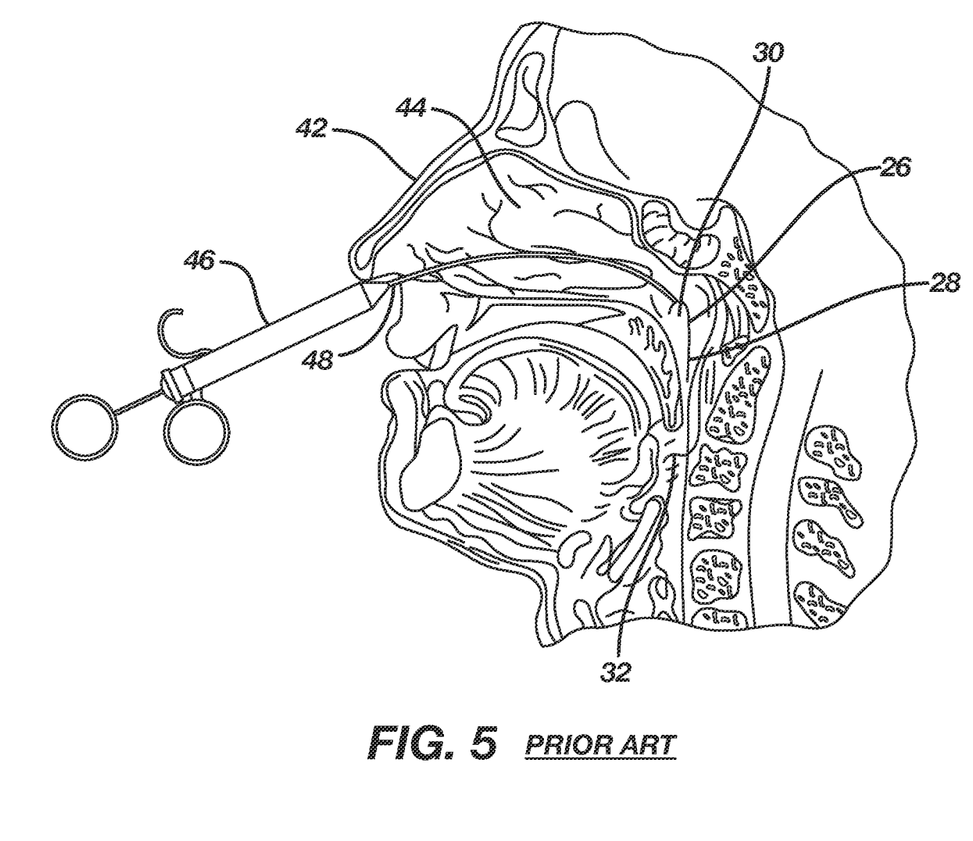
FIGS. 5-6 show a cross-section of a human head in the orientation shown in FIG. 2 showing a prior art politzeration method for relieving fluid in the middle ear in which a syringe is shown having a flexible tip extending into the nose and/or throat area so that the tip abuts the distal opening of the Eustachian tube while the nose is plugged.
Figure 6:
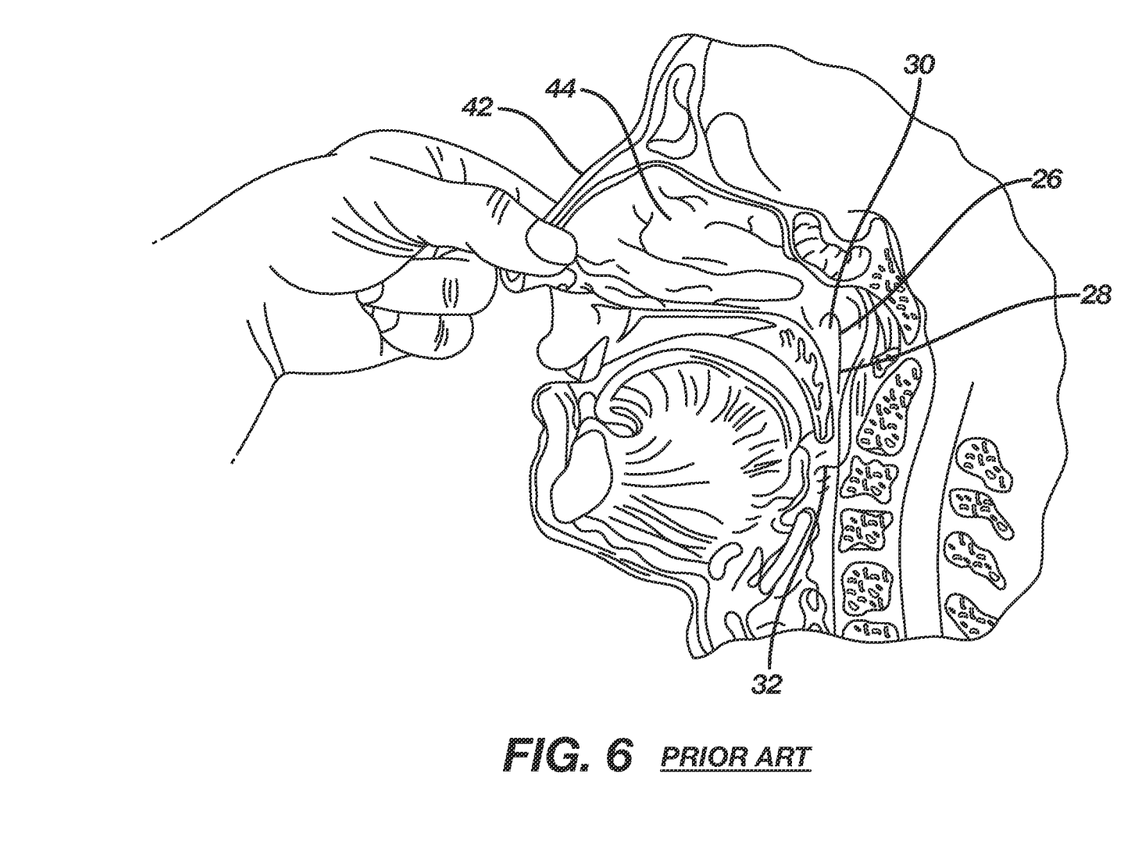

In connection with the above surgical treatments of FIGS. 3 and 4, Eustachian tube 26 inflation is also employed to relieve the pressure build-up and fluid accumulation as shown in FIG. 5. The hypodermic syringe 46 (shown with a flexible tip 48) is inserted into a nostril or into the mouth until the tip 48 is positioned adjacent the distal opening 28 of the Eustachian tube 26 in the nasopharynx region 30 of the throat 32. Air is blown through the tip 48 via the syringe 46 into the obstructed Eustachian tube 26 and, thus, into the middle ear 14 to help relieve the congestion and reestablish middle ear ventilation. This procedure is often referred to as politzerization. Politzerization is most effective when one of the nostrils is pinched shut (as shown in FIG. 6), while the patient simultaneously swallows. This procedure forces air into the Eustachian tube 26 and the middle ear 14. This technique is good for opening the Eustachian tube 26 but it does not clear accumulated fluid away.

Another method for clearing the middle ear 14 (at least temporarily) is referred to as the "valsalva" maneuver, accomplished by forcibly blowing air into the middle ear 14 while holding the nose, often called popping the ear. This method is also good for opening the Eustachian tube 26 but it does not clear the accumulated fluid away either.

Typical disorders associated with the middle ear and the Eustachian tube include perforated ear drums, tympanosclerosis, incus erosion, otitis media, cholesteotoma, mastoiditis, patulous Eustachian tube, and conductive hearing loss. To treat some of these disorders, ear surgery may be performed. Most ear surgery is microsurgery, performed with an operating microscope. Types of ear surgery include stapedectomy, tympanoplasty, myringotomy and ear tube surgery.

One of the simplest ear surgeries is the myringotomy or the incision of the ear drum. However, ear surgery can also require the removal of the tympanic membrane for the visualization of the middle ear space. Often surgeons will try to preserve the integrity of the membrane by making incisions in the skin of the ear canal and removing the tympanic membrane as a complete unit. Alternatively, middle ear access is achieved via the mastoids. This method approaches the middle ear space from behind the ear and drills through the mastoid air cells to the middle ear. Whether the bony partition between the external ear canal and the mastoid is removed or not depends on the extent of the disease. Canal-wall-down refers to the removal of this bony partition. Canal-wall-up refers to keeping this bony partition intact. The term modified radical mastoidectomy refers to an operation where this bony partition is removed and the eardrum and ossicles are reconstructed. A radical mastoidectomy is an operation where this bony partition is removed and the ear drum, malleus and incus bones are permanently removed so that the inner lining of the large cholesteotoma sac can be safely cleaned. This operation is done when an extensive cholesteotoma is encountered or one that is adherent to the inner ear or facial nerve.

Afflictions of the middle ear and Eustachian tube are very prevalent and a serious medical problem, afflicting millions of people and causing pain, discomfort and even hearing loss or permanent ear damage. Although a number of treatments have been developed, as described above each of them have shortcomings Therefore, a need exists for improved methods and systems for accessing, diagnosing and treating target tissue regions within the middle ear and the Eustachian tube. Ideally, such methods and systems would be minimally invasive and pose very little risk of damage to healthy ear tissue.

US Patent Publication No. 2010/0274188 which is incorporated by reference herein in its entirety is directed toward methods and systems for accessing, diagnosing and treating target tissue regions within the middle ear and the Eustachian tube. One particular method described in the publication is for dilating a Eustachian tube of a patient. A guide catheter may be advanced through a nasal passage of the patient to position a distal end of the guide catheter at or near an opening of the Eustachian tube of the patient. A distal portion of the guide catheter may include a bend having an angle between 30 and 90 degrees. The distal portion may be more flexible than a proximal portion of the guide catheter. A guidewire may be advanced through the guide catheter such that a distal end of the guidewire enters the Eustachian tube. A dilation catheter may be advanced over the guidewire to position a dilator of the dilation catheter within the Eustachian tube. The dilator may be expanded to dilate the Eustachian tube. The dilation catheter and guidewire may be removed from the patient.

Improvement in the devices described above would provide a system for dilation of the Eustachian tube that would be ergonomic and easy to use and would safely and effectively access the narrow Eustachian tube of a pediatric patient. Such systems would be compact for easy access of the Eustachian tube and excellent visualization thereof. Elimination of the need to incorporate a guide catheter or rigid endoscope in the system, but still allow for access through the tortuous anatomy and visualization thereof would be a desired aim of the invention.

SUMMARY OF THE INVENTION

The present invention provides systems and devices for accessing and treating the Eustachian tube of a patient.

In one aspect, the invention is directed to a system for use in accessing and dilating a Eustachian tube of a patient includes a flexible endoscope, balloon dilation catheter and a protective sheath for accessing and treating the Eustachian tube through the nose of a human patient. The system includes a protective sheath having an endoscope lumen and a balloon dilation catheter lumen, a flexible endoscope for use in visualizing the Eustachian tube of the patient within the endoscope lumen, and a balloon dilation catheter for accessing and treating the Eustachian tube within the balloon dilation catheter lumen. The balloon dilation catheter includes an elongate shaft, the elongate shaft having a proximal end and a distal end and an inflation lumen therebetween and a low profile inflatable balloon positioned at the distal end of the elongate shaft. The elongate shaft includes a hollow shaft portion extending from the proximal end of the elongate shaft to the inflatable balloon and a solid tube portion extending beyond the inflatable balloon.

In a second aspect, the invention is directed to a method for dilating a Eustachian tube of a patient. The method includes advancing the Eustachian Tube Dilation System into the nostril of a patient and through a nasal cavity to position a distal end of the system at, in or near an opening into the Eustachian tube. The method further includes visualizing the nasal cavity, the Eustachian Tube, and the balloon dilation catheter using the flexible endoscope, advancing the balloon of the balloon dilation catheter from the balloon dilation catheter lumen of the protective sheath to within the Eustachian tube, inflating the balloon to dilate the Eustachian Tube, deflating the balloon, optionally repeating the inflating and deflating step, withdrawing the balloon into the balloon dilation catheter lumen, and removing the Eustachian Tube Dilation System from the nostril of the patient.

In a third aspect, the invention is directed to a method for dilating a Eustachian tube of a patient. The method includes performing a myringotomy in a tympanic membrane of an ear of the patient, and advancing a balloon dilation catheter into or near an opening into the Eustachian tube. The method further includes advancing the balloon of the balloon dilation catheter to within the Eustachian tube, inflating the balloon to dilate the Eustachian Tube, deflating the balloon, optionally repeating the inflating and deflating step, and withdrawing the balloon dilation from the ear of the patient.

For a further understanding of the nature and advantages of the invention, reference should be made to the following description taken in conjunction with the accompanying figures. Each of the figures is provided for the purpose of illustration and description only and is not intended to limit the scope of the embodiments of the present invention.

DETAILED DESCRIPTION OF THE INVENTION

The following detailed description should be read with reference to the drawings in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" and "approximately" for any numerical values or ranges indicate a suitable dimensional tolerance that allows the part or collection of components to function for its intended purpose as described herein.

It will be appreciated that the terms "proximal" and "distal" are used herein with reference to a clinician gripping a handle. Thus, an end effector is distal with respect to the more proximal handle. It will be further appreciated that, for convenience and clarity, spatial terms such as "top" and "bottom" also are used herein with respect to the clinician gripping the handle. However, surgical instruments are used in many orientations and positions, and these terms are not intended to be limiting and absolute.

The embodiments of the present invention are directed toward methods and systems for easily accessing and treating target tissue regions within the middle ear and the Eustachian tube using a system that can provide for visualization of the Eustachian tube and dilation of the Eustachian tube without damaging structures in the middle ear.

Figure 7A:
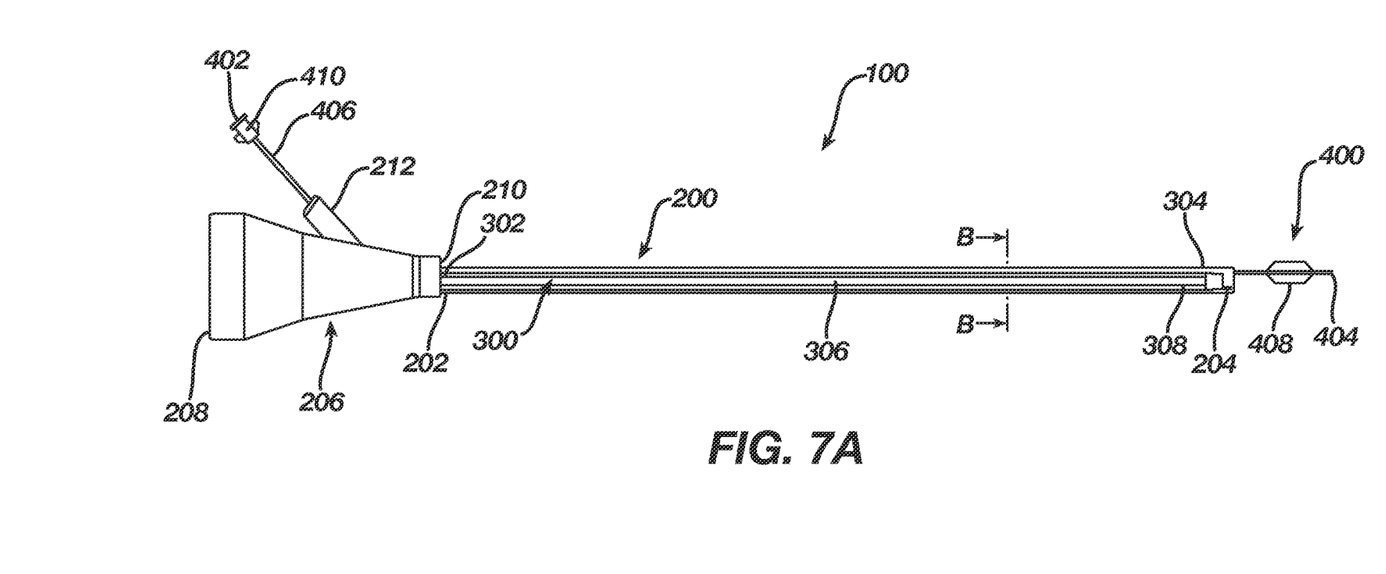
FIG. 7A is a simplified side view of a Eustachian tube dilation system according to the on embodiment of the invention including a protective sheath, flexible endoscope and balloon dilation catheter.

One embodiment of the Eustachian tube dilation system 100 of the invention is shown in FIG. 7A. As shown, the system 100 includes a protective sheath 200, a flexible endoscope 300 and a balloon dilation catheter 400. The protective sheath 200 includes a flexible shaft 216 that has a proximal end 202 and a distal end 204 and can be the Slide-ON® Endosheath System manufacture by Vision Sciences, Orangeburg, N.Y. The protective sheath 200 further includes a handle 206 through which the endoscope 300 and the balloon dilation catheter 400 can be inserted. The distal end 210 of the handle 206 is attached to the proximal end 202 of the flexible shaft 216. The flexible shaft 216 further comprises two lumens that extend from the proximal end 202 of the shaft 216 to the distal end 204 of the shaft, an endoscope lumen 218 and a working device lumen 220 (see FIG. 7B). The endoscope lumen 218 is closed at the distal end 204 of the flexible shaft 216 in order to protect the distal end 304 of the endoscope 300. The working device lumen 220 is open at the distal end 204 of the flexible shaft 216 to allow the distal portion 412 to extend beyond the distal end 204 of the flexible shaft 216. The flexible shaft 216 may be made of transparent, flexible polymeric material such as polyurethane, polyethylene, ethylene vinyl acetate and silicone in order to facilitate manoeuvrability of the system and visualization using the endoscope 300. The flexible shaft has a total length of between 20 cm and 60 cm, often between 20 and 30 cm or of between 50 and 60 cm. The handle 206 further comprises a side port 212 for insertion of a working device, in this case the balloon dilation catheter 400 as further described below. In an alternative embodiment, the side port for insertion of the balloon dilation catheter 400 may be positioned on the flexible shaft 216 of the protective sheath 200 such that the balloon dilation catheter 400 directly enters the working device lumen 220. In yet a further embodiment, a stiffening member surrounds the flexible shaft such that the Eustachian Tube dilation system can be easily inserted into the tortuous anatomy, but the flexible distal portion 308 of the endoscope 300 can be manipulated for visualization of the tortuous anatomy and proper placement of the balloon dilation catheter 400 within the Eustachian tube. The stiffening member has a total length of between 5 and 59 cm, often of between 5 and 25 cm or of between 35 and 55 cm. The sheath stiff section is located at a distance of between 8 mm and 15 mm from the distal end of the sheath.

The flexible endoscope 300 has a proximal end 302, a distal end 304 and a tubular body 306 therebetween. The flexible endoscope 300 may comprise any flexible endoscope known in the art including but not limited to the Flexible Rhino-fiberscope 3.5 mm×30 cm, 11101 RPA manufactured by Karl Storz, Tuttlingen, Germany. In use, the distal end 304 of endoscope 300 is inserted into the proximal end 208 of the handle 206 of the protective sheath 200, and into the endoscope lumen 218 such that the distal end 304 of the endoscope 300 is advanced to the distal end 204 of the flexible shaft 216 and the proximal end 302 of the endoscope 300 is seated within the handle 206 of the protective sheath 200. The distal portion of the endoscope may initially be used in the 0 degree position, but may be flexed up to a 90 degree position, often between 30 degrees and 55 degrees for visualization of the Eustachian tube. The angle of visualization can be customized according to the particular anatomy and age of the patient.

The balloon dilation catheter 400 has a proximal end 402, a distal end 404, an inflation shaft 406 between the proximal end 402 and the distal end 404, and an inflatable balloon 408. An inflation luer 410 defines the proximal end of the balloon dilation catheter 400.

Figure 7B:
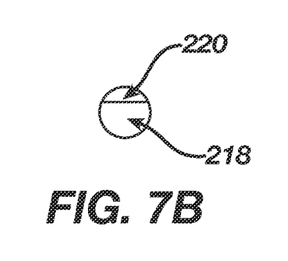
FIG. 7B is a cross-section view of the system of FIG. 7A taken at section A-A.
Figure 7C:
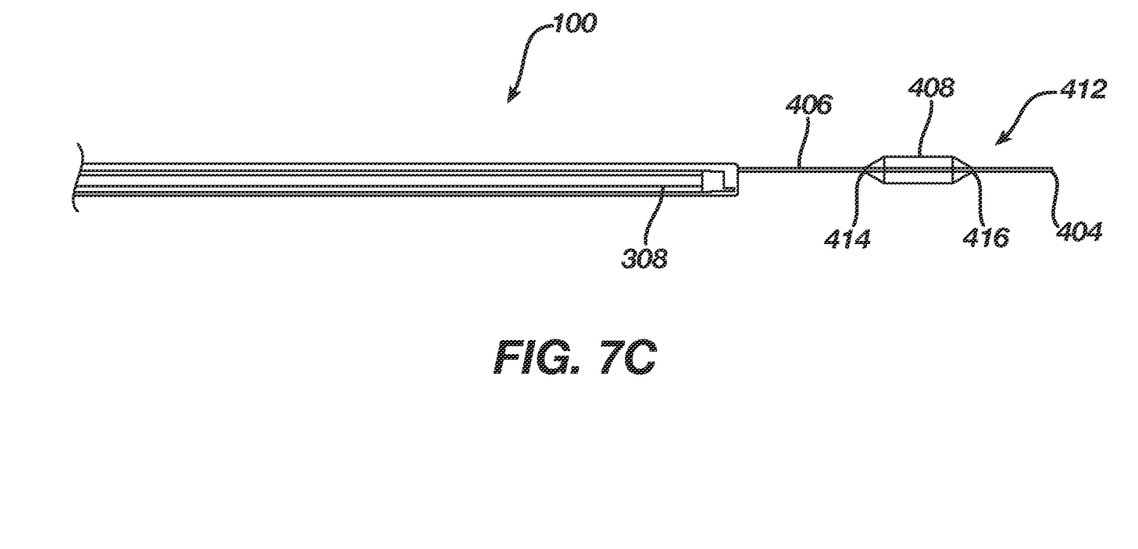
FIG. 7C is an enlarged view of the distal portion of the system shown in FIG. 7A.
Figure 8A:
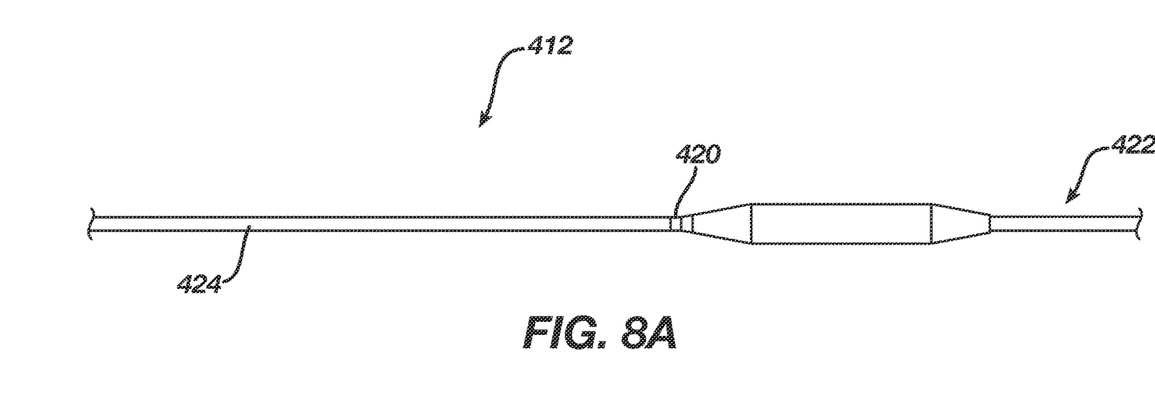
FIG. 8A is a simplified side view of a balloon dilation catheter portion of the system shown in FIGS. 7A-7C.
Figure 8B:
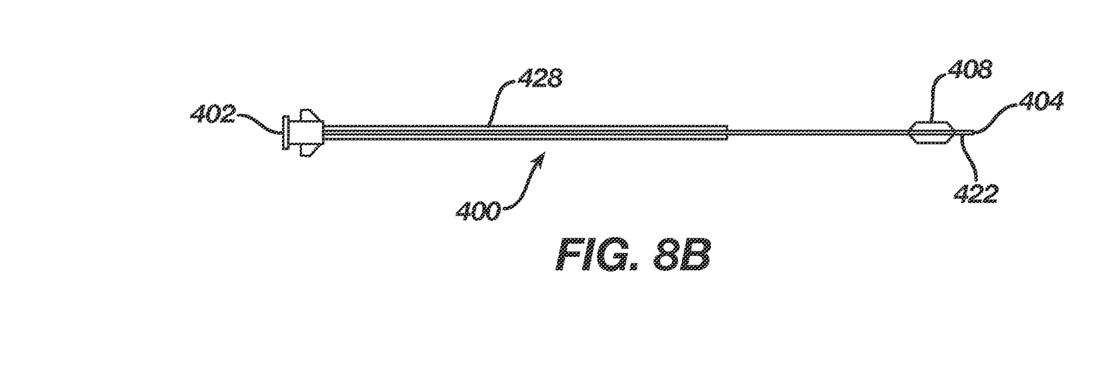
FIG. 8B is an enlarged view of the distal portion of the balloon dilation catheter shown in FIG. 8A.

The distal portion 102 of Eustachian tube dilation system 100 is shown in an enlarged view in FIG. 7C. The distal portion 412 of the balloon dilation catheter 400, that portion extending from the proximal end 414 of the dilation balloon 408 to the distal end of the 404 of the balloon dilation catheter 400 is shown in use as it extends beyond the distal end 204 of the protective sheath. In one embodiment, shown more clearly in FIGS. 8A and 8B, the balloon dilation catheter shaft 406 is an elongate shaft 406 that is made of a hollow superelastic material, such as a nitinol tube that includes a hollow inflation lumen 426 extending from the inflation luer 410 to the balloon 408 of the balloon dilation catheter 400, and further includes a solid tube extending from the distal end 416 of the balloon 408 to the distal end 404 of the balloon dilation catheter 400. The nitinol tube may be tapered, having a larger diameter (an outer diameter of 0.03 to 0.04 inches) near the proximal end of the system and a smaller diameter (0.001 to 0.01 inches) near the distal end of the system and may be laser cut to enhance flexibility. The elongate shaft 406 may be 50 cm to 75 cm in length often about 60 cm in length from the proximal end 402 to the distal end 404. Further a stiffening member 428 that in a particular embodiment may be a stainless steel hypotube, may be included at the proximal shaft portion 424 of the balloon dilation catheter 400 to ensure that the balloon dilation catheter 400 can be pushed into the Eustachian tube without kinking or buckling during insertion. In an additional embodiment of the balloon dilation catheter 400, the elongate shaft 406 may include a tapered core wire that is a solid tube with a larger diameter at its proximal end than at its distal and. Where the balloon dilation catheter is 64 cm in overall length, the tapered core wire may be 60 cm in overall length. The balloon dilation catheter may have a 48 cm polymeric (pebax) proximal section with an outside diameter of 0.054 inches, an inner diameter of the polymeric section of 0.040 inches, and an outside diameter of the core wire being 0.033 inches. The inflation lumen is a 0.007 inch lumen between the polymeric section and the core wire. The 16 cm distal section of the balloon dilation catheter includes an outer polymeric (pebax) tubing with an outside diameter of 0.034 inches, an inside diameter of 0.020 inches and a core wire of 0.005 inches, such that the inflation lumen is a 0.015 inches for rapid inflation and deflation of the balloon.

Where the core wire is 60 cm in overall length, the proximal portion of the core wire may have an outside diameter of 0.033 inches and may have a length of 24.6 cm. Moving distally, the next section may have be 14 cm long and may taper to an outside diameter of 0.014 inches. The next section may have a constant outside diameter of 0.014 inches and may be 6 cm long. The next, more distal section may be 9 cm long and may begin at an outside diameter of 0.014 inches and may taper to an outside diameter of 0.005 inches. The remaining distal end of the core wire is 6.4 cm long and has an outside diameter of 0.005 inches.

In an alternative embodiment, where the balloon dilation catheter is 32 cm in overall length, the tapered core wire may be 30 cm in overall length. The balloon dilation catheter may have a 24 cm polymeric (pebax) proximal section with an outside diameter of 0.054 inches, an inner diameter of the polymeric section of 0.040 inches, and an outside diameter of the core wire being 0.033 inches. The inflation lumen is a 0.007 inch lumen between the polymeric section and the core wire. The 8 cm distal section of the balloon dilation catheter includes an outer polymeric (pebax) tubing with an outside diameter of 0.034 inches, an inside diameter of 0.020 inches and a core wire of 0.005 inches, such that the inflation lumen is a 0.015 inches for rapid inflation and deflation of the balloon.

Where the core wire is 30 cm in overall length, the proximal portion of the core wire may have an outside diameter of 0.033 inches and may have a length of 12.3 cm. Moving distally, the next section may have be 7 cm long and may taper to an outside diameter of 0.014 inches. The next section may have a constant outside diameter of 0.014 inches and may be 3 cm long. The next, more distal section may be 4.5 cm long and may begin at an outside diameter of 0.014 inches and may taper to an outside diameter of 0.005 inches. The remaining distal end of the core wire is 3.2 cm long and has an outside diameter of 0.005 inches.

The tapered core wire is surrounded by a polymeric shaft. The polymeric shaft may be of uniform outside diameter, such that the inflation lumen, which is the lumen formed between the core wire and the polymeric shaft increases in size as the taper of the core wire decreases from the proximal end of the catheter shaft to distal end of the balloon dilation catheter. The core wire forms the distal tip 422 of the balloon dilation catheter which may be atraumatic, that is it soft and flexible such that it does not damage tissue in the tortuous pathway through which it is directed.

The balloon dilation catheter of the invention is shown in FIGS. 8A and 8B. The balloon dilation catheter 400 generally includes a polymeric (often pebax—polyether block amides, but may be of other materials of comparable strength and stiffness) elongate shaft 418 having a proximal end 402 and a distal end 404. The balloon dilation catheter 400 further includes a balloon 408 on the distal portion 412 of the elongate shaft 418. The balloon 408 may be a polymer balloon (compliant, semi-compliant or non-compliant). In one embodiment, the balloon may be a suitable non-compliant material such as but not limited to polyethylene terepthalate (PET), PEBAX, nylon or the like. The balloon catheter may include any low profile of balloon including but not limited to balloons with an outside diameter of less than 1.5 mm when deflated, and often between 1.0 mm and 1.5 mm when deflated. Size and shape of the balloon is chosen according to the age of the patients, and may have an outside diameter of less than 6 mm in diameter when inflated or of between about 2 mm and 4 mm when inflated. The balloon may have a working length of between and 10 mm and 14 mm, often of 12 mm in working length (for example 2 mm×12 mm, 3.5 mm×12 mm, 2 mm×10 mm and 3.5 mm×14 mm) The balloon catheter shaft may be coated with PTFE (Polytetrafluoroethylene) or other similar polymeric coating to enhance lubricity. The balloon dilation catheter 400 generally includes a proximally located connection, luer 410 for inflating/activating the balloon 408.

The balloon 408 may be expanded to dilate the Eustachian tube ET after it is placed in a desirable location therein. For example, the opening area of the Eustachian tube ET includes a pharyngeal ostium, and the dilation catheter 400 may be advanced to position the balloon in the pharyngeal ostium. The flexible endoscope 300 is used to assist in positioning the dilation catheter 400. The system 100 is advanced through the nasal passage to view the tortuous anatomy. A marker 420 on a shaft of the dilation catheter 400 can be viewed from the endoscope to approximate a location of the balloon 408 relative to the opening of the Eustachian tube ET based on a distance of the marker 420 from a proximal end of the balloon 408. Accordingly, the dilation catheter 400 can be moved to place the marker in a desirable location before expansion of the balloon 408 in the Eustachian tube ET.

In one embodiment, shown in FIGS. 8A and 8B, the distal end 412 of the balloon catheter 400 further includes a tip 422 and a stiff proximal shaft portion 424 that is constructed of a polymeric material including but not limited to pebax that extends from the proximal end of the elongate shaft 418 to the proximal end of the balloon 408. In one embodiment, the tip 422 may include a bulbous polymeric blueberry shaped tip that is atraumatic and is about 1.5 mm to 2 mm in length with an outer diameter of between about 2 mm and 3 mm. The smoothness and roundness of tip 422 facilitates advancement of the balloon catheter 400 by helping it glide smoothly through the Eustachian Tube ET. The tip further acts as a safety stop. The isthmus 29 of the Eustachian Tube, shown in FIG. 1 is approximately 1 mm in diameter. The tip diameter will prevent the balloon catheter 400 from passing through the isthmus 29 into the middle ear 14.

The balloon 408 may be held in location while in an expanded state for an extended period of time (e.g. several seconds or minutes). The balloon 408 may carry an expandable stent for delivery into the Eustachian tube upon expansion of the balloon 408. The balloon dilation catheter 400 and the guide catheter may be removed from the patient after the balloon 408 has been deflated/unexpanded. The Eustachian tube will resume functioning, normally opening and closing to equalize atmospheric pressure in the middle ear and protect the middle ear from unwanted pressure fluctuations and loud sounds.

The Eustachian Tube Dilation System 100 is assembled by inserting the flexible endoscope 300 into the endoscope lumen 218 of the protective sheath 200. The balloon dilation catheter 400 is then inserted into the working device lumen 220 of the protective sheath. The Eustachian Tube Dilation System 100 may be advanced into a nostril and through a nasal cavity with the endoscope 300 in a zero degree position to position a distal end of the catheter 400 at, in or near an opening into the Eustachian tube. The endoscope 300 is then steered to a 30 to 55 degree angle in order to point to the Eustachian tube opening prior to advancement of the balloon into the Eustachian tube. The low profile balloon dilation catheter of the invention is particularly designed for use in accessing the Eustachian tube, particularly the underdeveloped Eustachian tube of a pediatric patient. In one embodiment, the system 100 may be passed through a nostril to the Eustachian tube on the ipsilateral (same side) of the head. In an alternative embodiment, the system 100 may be passed through a nostril to the Eustachian tube on the contralateral (opposite side) of the head. The endoscope 300 is used to aid in accessing the Eustachian Tube.

After the system 100 is in a desired position, the balloon catheter 400 is advanced to position the balloon 408 of the balloon catheter 400 within the Eustachian tube. Following placement of the balloon catheter into the desired position any number of procedures may be carried out. The inflation lumen 426 is used for inflation of the balloon 408 with water, contrast medium or saline through inflation port 410 to a pressure of between about 3 and 15 atmospheres. One or more dilations may be carried out before the balloon dilation catheter is withdrawn into the balloon dilation catheter lumen of the protective sheath, the angle of the endoscope is returned to 0 degrees, and the system is removed from the patient's anatomy.

Alternatively, in view of the narrow profile and flexibility of the balloon dilation catheter of the invention, the balloon dilation catheter may be advanced through a myringotomy that has been made in the tympanic membrane. The balloon dilation catheter distal end will include an atraumatic tip such that it can be advanced through the myringotomy, which has been previously made in the tympanic membrane, and can be advanced through the middle ear 14 and the bony isthmus 29 and into the Eustachian Tube. The inflation lumen 426 is used for inflation of the balloon 408 with water, contrast medium or saline through inflation port 410 to a pressure of between about 3 and 15 atmospheres. One or more dilations may be carried out before the balloon of the balloon dilation catheter is deflated and the dilation catheter is withdrawn from the anatomy.

While preferred embodiments of the present invention have been shown and described herein, it will be obvious to those skilled in the art that such embodiments are provided by way of example only. Numerous variations, changes and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A method for dilating a Eustachian tube of a patient, the method comprising:

advancing a Eustachian Tube Dilation System into a nostril of the patient and through a nasal cavity to position a distal end of the Eustachian Tube Dilation System at, in or near an opening into the Eustachian tube, the Eustachian Tube Dilation System comprising:
a protective sheath comprising a flexible elongate shaft, an endoscope lumen and a balloon dilation catheter lumen;
a stiffening member surrounding the flexible elongate shaft of the protective sheath;
a flexible endoscope for use in visualizing the Eustachian tube of the patient within said endoscope lumen;

a balloon dilation catheter for accessing and treating the Eustachian tube with said balloon dilation catheter lumen, wherein the balloon dilation catheter comprises:
- an elongate shaft, the elongate shaft having a proximal end and a distal end and an inflation lumen therebetween;
- a low-profile inflatable balloon positioned at the distal end of said elongate shaft; wherein the elongate shaft comprises a hollow shaft extending from the proximal end of the elongate shaft to the inflatable balloon, and a solid shaft extending beyond the inflatable balloon;

visualizing the nasal cavity, the Eustachian Tube, and the balloon dilation catheter using the flexible endoscope;

advancing the balloon of the balloon dilation catheter from the balloon dilation catheter lumen to within the Eustachian tube;

inflating the balloon to dilate the Eustachian Tube;

deflating the balloon;

optionally repeating the inflating and deflating step;

withdrawing the balloon into the balloon dilation catheter lumen; and removing the Eustachian Tube Dilation System from the nostril of the patient.

2. The method of claim 1 wherein the hollow shaft comprises a shape memory material.

3. The method of claim 1 wherein the hollow shaft comprises a polymeric material and wherein the solid shaft further comprises a core wire extending from the elongate shaft proximal end.

4. The method of claim 3 wherein the core wire has a proximal end and a distal end and the core wire is tapered such that the proximal has a greater diameter than the distal end.

5. The method of claim 1 wherein the protective sheath further comprises a handle for insertion of the endoscope and the balloon dilation catheter.

6. The method of claim 5 wherein the handle further comprises a side port for insertion of the balloon dilation catheter.

7. The method of claim 6 wherein a side port is positioned on the flexible elongate shaft for insertion of the balloon dilation catheter directly into the balloon dilation catheter lumen.

8. The method of claim 1 wherein the low-profile balloon comprises a balloon with an outside diameter of between 1.0 mm and 1.5 mm when deflated and 2.0 mm and 3.5 mm when inflated.

* * * * *